United States Patent [19]
*Martin et al.

[11] Patent Number: 5,737,056
[45] Date of Patent: Apr. 7, 1998

[54] METHOD FOR SIMULATION OF VISUAL DISABILITIES

[75] Inventors: Neil F. Martin, Potomac; Terese W. Robinson; Howard N. Robinson, both of Lutherville, all of Md.

[73] Assignee: Bloom & Kreten, Towson, Md.; 14; a part interest

[*] Notice: The term of this patent shall not extend beyond the expiration date of Pat. No. 5,495,305.

[21] Appl. No.: 593,879

[22] Filed: Jan. 30, 1996

Related U.S. Application Data

[63] Continuation-in-part of Ser. No. 331,029, Oct. 27, 1994, Pat. No. 5,495,305.

[51] Int. Cl.$^6$ .............................. G02C 7/10; G02C 7/02
[52] U.S. Cl. .............................. 351/177; 351/45; 351/47; 351/159; 351/165
[58] Field of Search .............................. 351/159, 165, 351/172, 177, 45, 47

[56] References Cited

U.S. PATENT DOCUMENTS

| | | | |
|---|---|---|---|
| 3,536,386 | 10/1970 | Spivack | 351/160 |
| 4,405,216 | 9/1983 | Nadler et al. | 351/237 |
| 4,498,743 | 2/1985 | Feinbloom | 351/45 |
| 4,698,022 | 10/1987 | Gilson | 351/47 |
| 4,890,911 | 1/1990 | Sulc et al. | 351/160 |
| 4,966,452 | 10/1990 | Shields et al. | 351/219 |
| 4,976,533 | 12/1990 | Hahn et al. | 351/160 |
| 5,009,497 | 4/1991 | Cohen | 351/161 |
| 5,062,701 | 11/1991 | Drazba et al. | 351/160 |
| 5,100,226 | 3/1992 | Freeman | 351/160 |
| 5,278,592 | 1/1994 | Marie et al. | 351/160 |
| 5,372,504 | 12/1994 | Buechler | 351/47 |

OTHER PUBLICATIONS

Wilson–Ocular Surgery News, Jan. 15, 1994, p. 35.
Colgan–Ocular Surgery News, May 1, 1995, p. 10.
Overmyer–Ophthalmology Times, May 1–7, 1995, p. 14.

*Primary Examiner*—Scott J. Sugarman
*Attorney, Agent, or Firm*—Leonard Bloom

[57] ABSTRACT

The disclosed invention is directed to lenses to be worn with eyeglasses. The light transmission or field of vision of the lenses has been so modified as to produce visual distortions simulating various eye conditions and particularly simulated possible postoperative visual distortions and anomalies. Various modifications to conventional eyeglasses are disclosed.

4 Claims, 15 Drawing Sheets

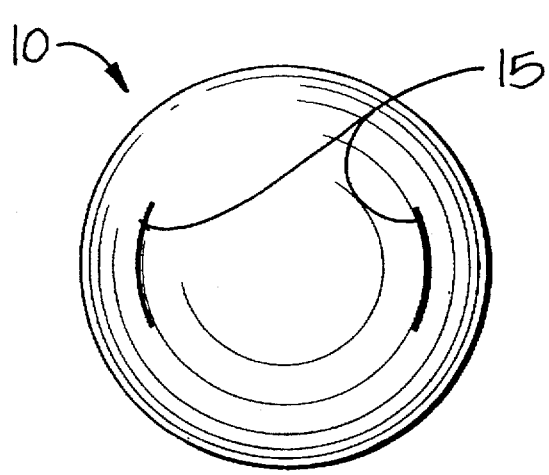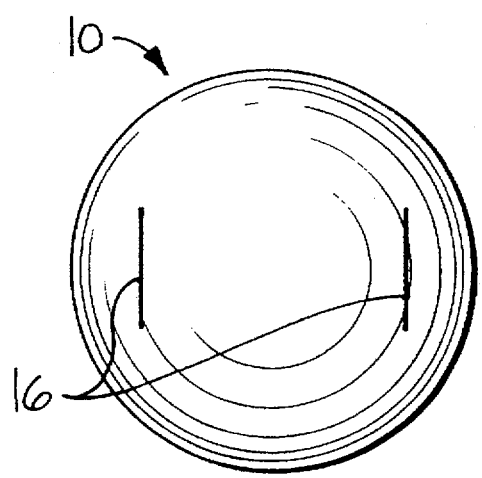

METHOD FOR SIMULATION OF VISUAL DISABILITIES

CROSS REFERENCE TO RELATED APPLICATION

The present invention constitutes a continuation-in-part of Ser. No. 08/331,029 filed Oct. 27, 1994, now U.S. Pat. No. 5,495,305, the disclosure of which is incorporated herein in its entirety.

FIELD OF THE INVENTION

The invention is concerned with the simulation of visual disturbances with the use of specially produced contact lenses, as well as specially constructed eyeglasses, and eyeglass modifications.

BACKGROUND OF THE INVENTION

Medical diseases of the eye—as well as eye surgery, such as refractive surgery—can create post-operative visual disturbances for the patient. Because of this post-operative risk of visual disturbance, informed consent from the patient to the doctor is essential. As part of the presently practiced method of informed consent required from the prospective patient prior to surgery, the doctor describes to the patient what visual anomalies to expect as a result of the surgery. This description is open to subjective interpretation by the patient, and in many instances the information conveyed to the patient by the doctor is inadequate and is misinterpreted by the patient.

Significant visual distortions may commonly occur with cataracts and macular degeneration which, respectively, are the leading causes of treatable and nontreatable blindness in the United States. These diseases affect millions of patients and the visual difficulties suffered by the patients are sometimes difficult for medical personnel and the families of patients to understand and appreciate.

Additionally, new refractive procedures, radial keratotomy (RK) and its related surgery, astigmatic keratotomy (AK) and excimer laser photorefractive keratectomy (PRK), are being performed on growing numbers of patients. Radial Keratotomy (RK) and excimer laser photokeratotomy (PRK) are the dominant surgeries for the correction of refractive errors of the eye. It is estimated that approximately 300,000 to 500,000 RK procedures were performed in the U.S., and 250,000 to 300,000 PRK procedures were performed world wide during the year 1993. These surgeries are performed to correct myopia (near-sightedness) and astigmatism. Alone, myopia affects at least thirty percent of the population of the U.S. and higher proportions of the population in Far Eastern countries. PRK is also undergoing clinical trials, and approximately one million myopes will undergo PRK yearly in the U.S. once the procedure is finally approved by the FDA. PRK also shows promise for the correction of hyperopia (farsightedness).

Other refractive procedures are undergoing development which may extend the applicability of refractive surgery. These procedures include intra-lamellar corneal rings, automated lamellar keratectomy (ALK), intrastromal photoablation and "flap and zap" (ALK combined with PRK). All of the foregoing refractive procedures have the potential for reducing visual acuity and/or creating optical aberrations. Obtaining good (and legal) preoperative informed consent from patients undergoing these procedures, especially where there is an increasing amount of advertising relating to such surgery, is necessary and important. This is so because there is potential for postoperative permanent visual degradation from glare and loss of contrast sensitivity. Unmet patient expectations can create disappointment and anger and can lead to malpractice suits, even when good post-operative results are obtained.

SUMMARY OF THE INVENTION

The main purpose of the present invention is to simulate some of the visual problems which may be encountered in refractive surgery (especially, starbursting with RK and glare with PRK). This simulation of visual problems will enhance the level of patient education, and communication between doctor and patient, in obtaining legally sufficient informed consent. Since visual distortions are phenomena that are difficult to explain, the invention provides great benefit to the patient, as well as the doctor, since the patient can be objectively apprised of how the surgery could affect post-operative vision. The herein disclosed invention provides methods for the patient to effectively assess the result of prospective surgery, so that he or she might have a means of evaluation based on his or her own physiological response.

With all this in mind, the inventors have provided a series of modified contact lenses, eyeglasses and eyeglass modifications which when worn by a patient will produce the type of postoperative visual distortions that could be expected, in some cases, as a result of various types of eye surgery. Having worn the eyeglasses, eyeglass modifications or lenses, and having actually experienced the visual distortion that could be produced as a result of surgery, the patient can make an educated judgment and give informed consent to the doctor prior to having surgery performed on the eye or eyes. Since the patient has worn the lenses and experienced visual distortion, he or she is less likely to complain to the doctor about any post-operative visual anomaly.

In addition to being useful for providing informed consent, the lenses of this invention also have educational uses. The lenses simulating visual disturbances and disease have significant educational utility for medical students and nurses in the classroom, as well as for doctors in practice. The lenses can be used to educate families of patients with ocular disease regarding the patient's pre-operative visual distortions, as well as possible post-operative visual anomalies; all of this with a specific view of letting the families know what can be expected as a result of surgery. Besides postoperative anomalies, among the disease conditions that may be simulated by the lenses of this invention are the various manifestations of cataracts, corneal opacities, retinal detachments, possibly macular degeneration, as well as hemi- and quadrantanopias.

The basic contact lenses (CL) used in this invention are produced in a seemingly limitless assortment of curvatures and thickness to meet individual prescription fitting requirements. The lenses are made of a variety of materials, such as hydrogels containing varying amounts of water. Lenses with less than 50% water content are considered to be "low water" lenses. The surface characteristics of the lens can vary. Less reactive surfaces are termed "nonionic" and more reactive surfaces are labeled "ionic". To satisfy cosmetic, as well as prescription requirements of patients, lenses are produced in a variety of colors, such as blue, green, brown, etc. The technology for placing markings on contact lenses is known in the art.

The present invention modifies existing contact lenses in a variety of ways to create optical post operative or disease abnormalities. The lens can be modified with lines or areas that are laser marked or etched. The markings can be molded, painted or dyed onto the surface of soft, hard or gas permeable hard contact lenses. Current lens manufacture routinely incorporates either laser engraving or molding of logos and lens parameters into the margins of soft contact lenses. This same technology can be used to make the lens markings on the lenses of this invention. Soft contact lenses are also frequently painted with opaque colors or transparent dyes to simulate various eye colors. These techniques may be employed to affect the light coming through the contact lens(es) and to create various optical characteristics. More specifically;

1. The glare and nocturnal starbursting experienced in RK may be created with six or eight radial laser marks that extend slightly within the pupillary margin. Small optical zones are frequently employed in RK (2.75 mm) and similar specifications may be used in the current invention. (See drawings)

2. The glare experienced with PRK may be simulated by a slight hazing of the central, 3 to 6 mm of the contact lens.

3. Macular degeneration and cataracts may be simulated by darker or more intense central (optical zone) alteration of the contact lens.

The simplest embodiment of this invention will be based upon using soft contact lenses ("SCL's"), although hard contact lenses ("HCL's"), rigid gas permeable contact lenses ("RGP's"), silicone lenses and hybrid lenses (RGP center and SCL surround, as in the Saturn lenses) may be used. The lenses can be manufactured in any refractive power to fit the patient's individual refractive need and the degree of optical-simulating modification can be titrated with the amount of optical correction (e.g. higher power RK simulating lenses would have more central radial lines, and higher power PRK lenses would have more central haze). A possible embodiment would be an ultrathin lens (such as the CSIT-™) with no optical power (plano) over which the patient could wear his/her contact lenses piggyback style. Soft contact lenses could be provided as disposable lens.

Macular degeneration would be capable of simulation with a zone of near total opacity (nearly 0% transmission) that would be slightly smaller than the person's pupil. As is well known, pupil size varies with age and is larger at younger age. Pupil size may be 5 to 8 mm in a younger person and 2 to 3 mm in older individuals. The proper size of the central opacity in the contact lens (CL) would be about 4 mm for patients in their twenties to thirties.

It should be possible to simulate visual fields defects from neuro-ophthalmic conditions of the visual pathways such as:

1. optic neuropathies (central scotoma (blind spot) or altitudinal defect (half of the vision obscured above or below a central horizontal meridian through fixation);

2. hemianopia (half of the vision obscured in both eyes together along a vertical meridian through fixation) either homonymous (same side in both eyes) or heteronomous (opposite sides for both eyes—either bitemporal or binasal).

Central scotomas would be simulated by an absolute central CL opacity just smaller than the pupil and field defects would be simulated by opacity covering a half or a quarter of the CL extending through the center of the CL and covering a significant area of the lens (larger than the pupil to perhaps the size of the cornea, 11 to 12 mm). Optically, one may find that central opacities that are larger than the pupil may still allow light to enter the eye as peripheral light rays striking the cornea are refracted toward the pupil by the convex surface of the cornea. Specified opacity and size of opacity relative to the pupil size may require some experimentation to determine the optimum lens modification and therefore need some leeway until actual CL(s) are manufactured and tried clinically on the patient. As a specific modification the opaque CL areas may be oriented by using CL(s) that are toric or are truncated or have a configuration that provides ballast.

As a special embodiment of this invention, eyeglasses (spectacles) are modified so that their lenses are constructed so as to have modifications similar to the modifications on the contact lenses.

An important embodiment of the present invention is a disposable soft contact lens with laser or molded marks. The lens may be made very thin to be worn under (or over) the patient's own contact lenses (piggy back style) or under the patient's eyeglasses. In a preferred embodiment of this invention, the patient's prescription contact lens may be used to make the etched or marked lens.

In its broadest aspect, this invention involves a contact lens useful for simulating an ophthalmologic anomaly (as exemplified throughout this specification) which may be the post-operative result of surgery, comprising a lens whose field of vision has been modified to simulate said ophthalmologic anomaly. Said contact lens can be one whose light transmission has been modified to produce the glare and nocturnal starbursting experienced in radial keratotomy. The glare and nocturnal starbursting can be produced by four, six or eight radial marks that extend slightly within the pupillary margin.

As an alternative embodiment, the light transmission of the contact lens has been modified to produce the glare experienced after photorefractive keratectomy. In this embodiment the glare can be produced by a slight hazing of the central portion of the contact lens. In another embodiment the hazing is of 3 to 6 mm of the central portion of the contact lens.

The invention herein described is most concerned with a method for obtaining informed consent from a patient prior to surgery by fitting the patient with a device, the field of vision of which has been modified to simulate the ophthalmologic anomaly which might be experienced by the patient as a result of said surgery. The modified device can be a contact lens, an eyeglass or a pair of eyeglasses.

An important method of obtaining informed consent from a patient prior to surgery comprises fitting the patient with a virtual reality device which has been programmed to simulate the ophthalmologic anomaly which might be experienced by the patient as a result of said surgery, and then obtaining informed consent.

Other significant embodiments of devices for simulating visual anomalies are envisioned by the inventors. Among the embodiments contemplated are clip-on lenses which would fit over the patient's glasses; alternative to the clip-on lenses, the lenses could be such as would slide behind the lenses of the patient's eyeglasses.

Another embodiment contemplated by the inventors is a modified thin transparent film that can be pressed onto the lenses of eyeglasses or spectacles. This modified thin transparent film press-on has markings thereon, such that when the film is applied to a lens of eyeglasses, the markings thereon will create in the field of vision of the eyeglasses an ophthalmologic anomaly.

A still further embodiment embraces a hinged visor or loupes which would be fitted over eyeglasses and produce the visual anomaly.

In each embodiment set forth above, the line of vision of the device, (e.g., contact lenses, eyeglasses, clip-on lenses or thin film press-on lenses), has been modified to produce the visual anomaly. And more specifically, for example, the field of vision on the lenses have been modified to simulate star-bursting or hazing, etc.

In its broadest aspect this invention encompasses a modified lens designed to be worn in conjunction with eyeglasses and used for obtaining informed consent from a patient. The lens has a field of vision which has been modified to simulate an ophthalmologic anomaly which may be the post-operative result of surgery. The modified lens when worn by a patient in conjunction with said eyeglasses will produce a visual anomaly and allow the patient to give the doctor competent informed consent. The modified lens can be contained in a loupe; or the lens can be contained in clip-on glasses, hinged clip-on glasses or slide-behind glasses.

The modified lenses as a pair are designed to be worn in conjunction with eyeglasses. The lenses have their field of vision modified to simulate an ophthalmologic anomaly which may be the post-operative result of surgery. The modified pair of lenses can be contained in clip-on glasses, hinged clip-on glasses or slide behind glasses.

Eyeglasses with at least one modified lens are designed to be worn in conjunction with a second pair of eyeglasses, and will allow the patient to give the doctor competent informed consent. The eyeglasses may be slide behind glasses or eyeglasses having a clip or a hinged clip designed to be attached to a second pair of eyeglasses, and when worn with said second pair of eyeglasses will allow the patient to give the doctor competent informed consent.

This invention envisions a modified thin transparent film press-on to be applied over the lens of eyeglasses and is useful in simulating an ophthalmologic anomaly which may be the postoperative result of surgery. The modified thin transparent film has markings such that its field of vision is modified to simulate said ophthalmologic anomaly, and when applied over the eyeglass lens of a patient will allow the patient to give the doctor competent informed consent.

The thin film can be made of plastic and is shaped to be able to fit onto the surface of an eyeglass. More specifically, the thin film is flexible plastic with a surface coated with adhesive to allow it to adhere to an eyeglass lens.

In ultimate use the lenses and eyeglasses of this invention are to be used for obtaining informed consent from a patient prior to ophthalmologic surgery. The method of use would comprise fitting over eyeglasses worn by said patient a lens or lenses whose field of vision has been modified to simulate a visual anomaly which may occur as a result of said surgery and then obtaining informed consent from said patient.

BRIEF DESCRIPTION OF THE DRAWINGS

FIG. 9 is a front elevational view of the contact lens with paired arcuate cuts.

FIG. 10 is a front elevational view of the contact lens with paired "T-cuts".

DESCRIPTION OF THE PREFERRED EMBODIMENTS

Figure 1:
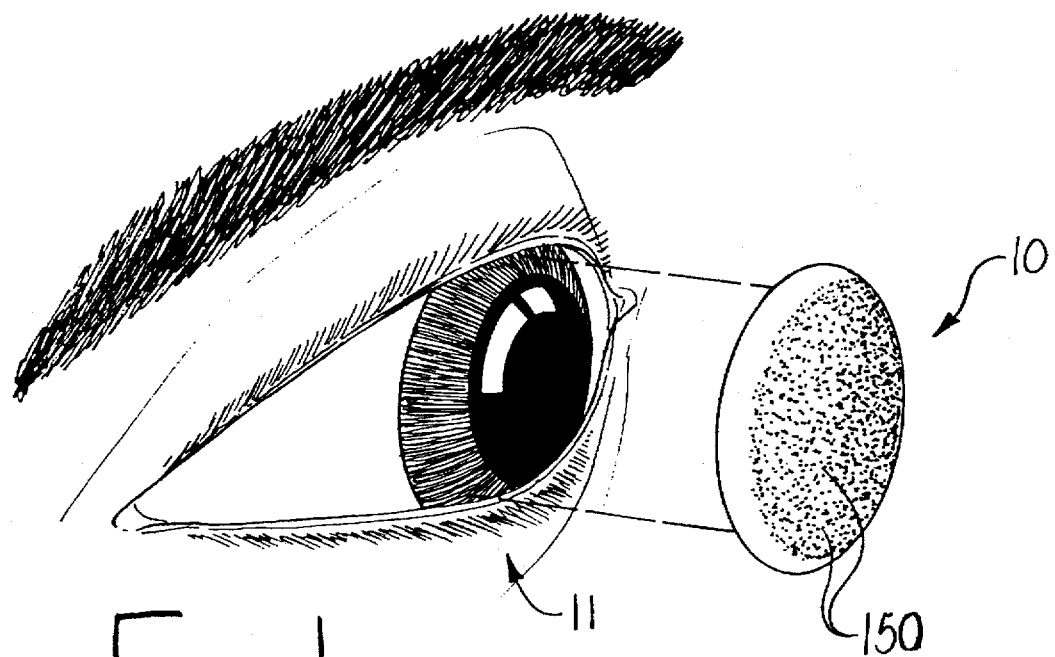
FIG. 1 is a perspective view of the contact lens of this invention about to be fitted into the eye. The contact lens having eight radial lines.

With reference to FIG. 1, a contact lens 10 of this invention about to be fitted into the eye 11 has eight radial lines 12. The contact lens 10 with radial lines 12 when worn will simulate glare and nocturnal starbursting, a visual anomaly which may result from radial keratotomy (RK).

Figure 2:
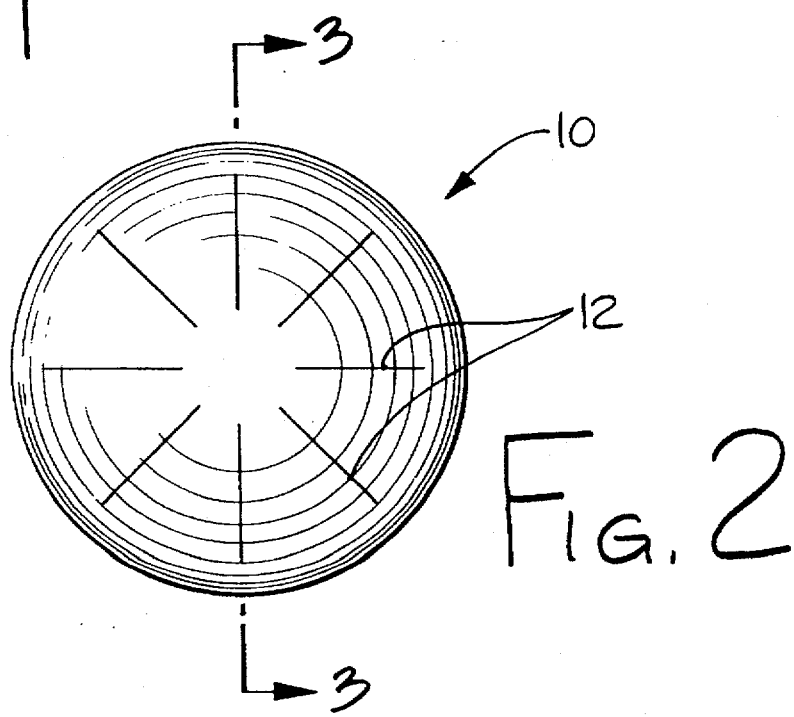
FIG. 2 is a front elevational view thereof.
Figure 3:
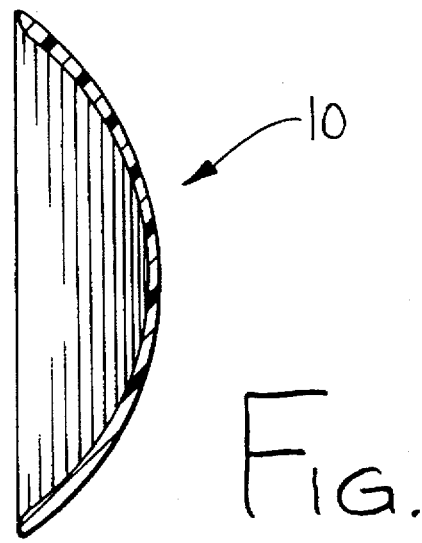
FIG. 3 is a cross-sectional view taken along lines 3—3 of FIG. 2.

The contact lens 10 can be a conventional contact lens 10 (FIGS. 2 and 3) which has had its field of vision modified by etching, dying, etc. to form the lines 12 or other contemplated configurations (FIG. 2).

Figure 4:
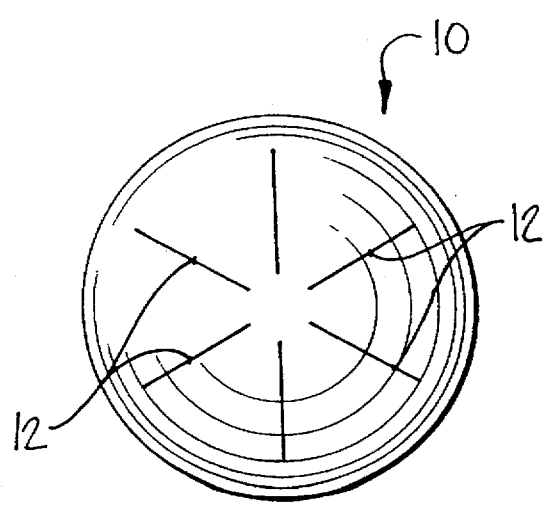
FIG. 4 is a front elevational view of the contact lens with six radial lines.
Figure 5:
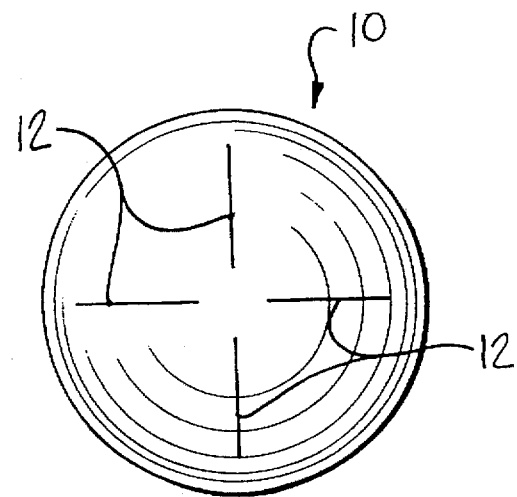
FIG. 5 is a front elevational view of the contact lens with four radial lines.

The contact lens 10 to simulate glare and nocturnal starbursting may have a varying number of radial lines 12. FIGS. 2, 4 and 5 are examples of lenses 10 with radial lines 12 producing varying degrees of glare and nocturnal starbursting.

In the case of RK, the visual effects of the lenses 10 are created by making radial lines 12 on or in the lenses 10 in the same patterns that are incised into the cornea in performing RK. Four, six or eight radial lines 12 would be made with optical zones of 1.75 to 5.0 mm (RK optical zone range) extending toward the rim of the lens to a diameter of from 10 to 12 mm. The lines 12 would be 0.1 to 1.0 mm wide and white in color. The lines would most ideally be laser etched onto the soft contact lens (SCL) or the lines could be fine ridges or depressions molded into the lens when manufactured. Opacity could be created by molding fine cross hatching, dimples or parallel lines in the same dimensions used by lens manufacturers when imprinting SCLs with parameter and brand logo indicators. Height or depth of molded lines are in the tenths of mm. Hatching, etc. would be in the hundredths to tenths of mm (ex. illustration of B&L disposable lens). Alternatively, various lines and patterns can be painted on the surface of the lens (like in opaque colored cosmetic contacts) or dyed onto the lens or created with a photo engraving process. Ideally, the lines 12 should extend through the substance (e.g., plastic) of the CL to give some of the depth such as actual RK scars exhibit. Actual scars are 100% of the corneal thickness as measured in the para central zone by ultrasound contact pachymetry (0.500 mm +/–0.100 mm).

Figure 6:
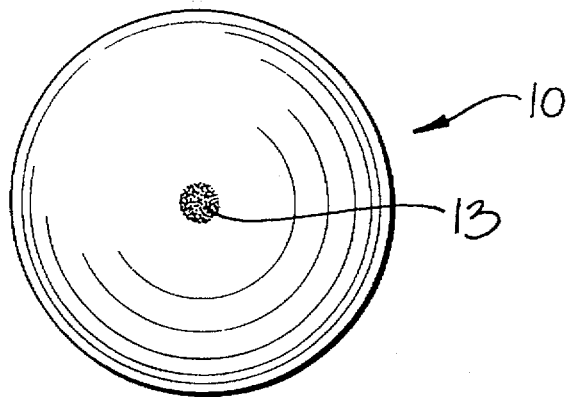
FIG. 6 is a front elevational view of the contact lens with slight hazing.

The glare which may be experienced after photorefractive keratectomy (PRK) may be simulated by a slight hazing 13 of the central 3 to 6 mm of the contact lens 1 (FIG. 6).

In the case of PRK, the central cornea is ablated with an excimer laser in an optical zone of 6.0 mm +/–2 mm to achieve a central flattening to correct myopia. As the cornea heals, this area may develop a fine reticular haze that may take several months to fade and may be permanent. This haze gives a glare, slight blur or a loss of contrast sensitivity. The effect of the haze is most prominent at night when bright oncoming lights may give a glary "dirty windshield" effect. To simulate the optical aberrations of PRK the 6.0 +/–2 mm optical zone of the SCL would be modified to create a fine hazy pattern similar to that of healing cornea. Actual photographic examples of clinical haze may be used as models to determine the degree of opacity. The front surface of the contact lens may be modified to create the anterior irregular astigmatism that develops as the cornea epithelium heals and the regeneration of new stromal collagen occurs. Central corneal islands (irregular areas of ablation) may be simulated by the contact lens, as well. If there are measurements or units of light scatter used in physical optics, the required amount or degree would be mild in the case of PRK modeling (as compared to say cataracts where significant scatter/opacity would be indicated). Techniques similar to those used for the RK SCL could be employed e.g., molding, laser etching, dying, painting or photographic processes.

Figure 7:
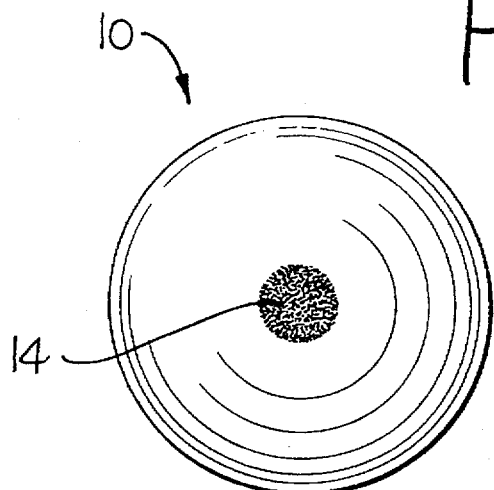
FIG. 7 is a front elevational view of the contact lens with moderate hazing.
Figure 8:
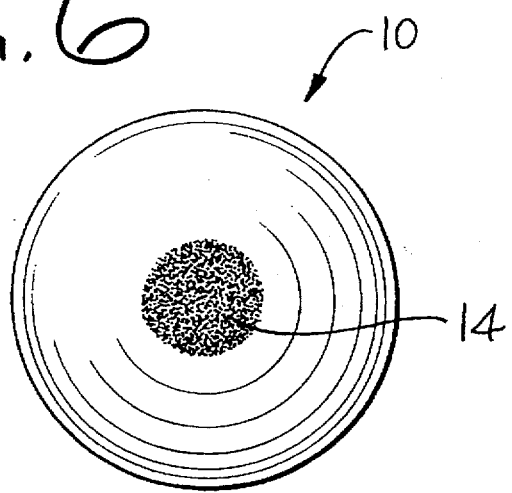
FIG. 8 is a front elevational view of the contact lens with substantial hazing.

Macular degeneration and cataracts may be simulated by darker or more intense central (optical zone) hazing 14 of the contact lens 1 (FIGS. 7–8).

With reference to FIG. 9 a lens 10 with paired arcuate cuts 15 approximately 6 mm apart; and with reference to FIG. 10 paired "T-cuts" 16 approximately 6 mm apart. The lenses of FIGS. 9 and 10 are of a size to cover the cornea. Arcuate 15 or T-cuts 16 for AK could be simulated (astigmatic cuts), although these cuts would probably be less useful since they would be as pairs 180 degrees apart, at a 6 mm optical zone (and 30 to 90 degree extent), and may be far enough away from the optical zone that they would not create much visual effect.

Other medial opacities, such as corneal scars, corneal edema or cataracts, could be simulated by creating central optical zone haze 14 or opacity of denser magnitude to decrease light transmission and increase light scatter. [Scatter effects would be more important than reducing light transmission; as sun glasses that have only 50% or 10% transmission may allow persons with normal vision to still see satisfactorily.] Sufficient haze to reduce vision to say 20/50 or 20/60 would demonstrate moderate clinically significant disease and reductions to 20/200 or 20/400 would demonstrate advanced opacities. Wedge-shaped clefts, variable opacity and brown discoloration in the lenses would produce an effect similar to actual cataracts.

Figure 11:
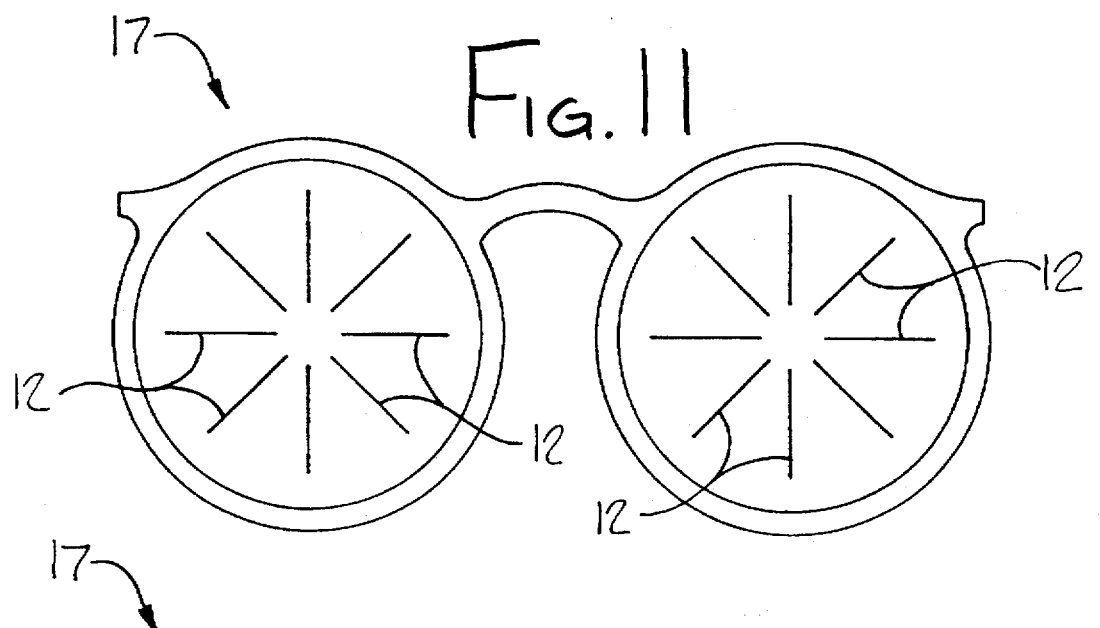
FIG. 11 is an elevational view of eyeglasses with lenses marked with radial lines.
Figure 12:
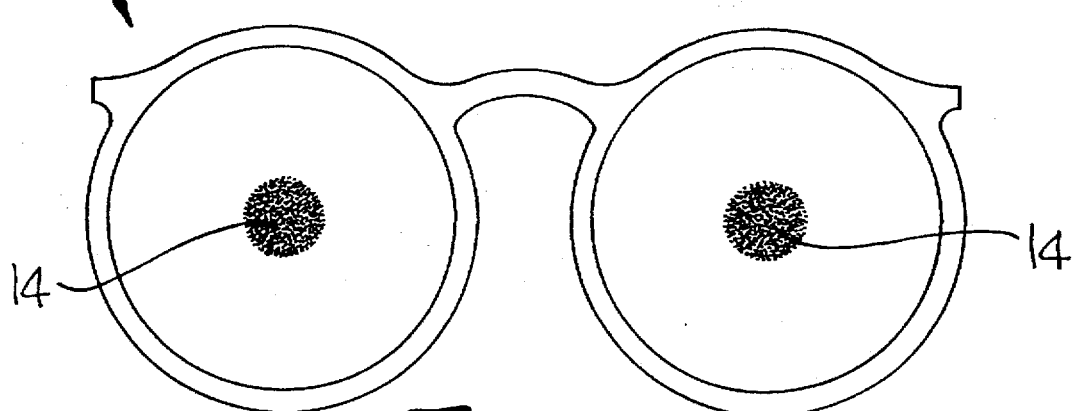
FIG. 12 is an elevational view of eyeglasses with central hazing.

There are times when the patient will not be able to wear contact lenses. With this being the case this invention supplies eyeglasses 17 with various markings simulating visual anomalies (FIGS. 11–12). FIG. 11 simulates starbursting and the hazing 12, and FIG. 12 simulates glare 14 which may be experienced after RK and PRK, respectively.

Figure 13:
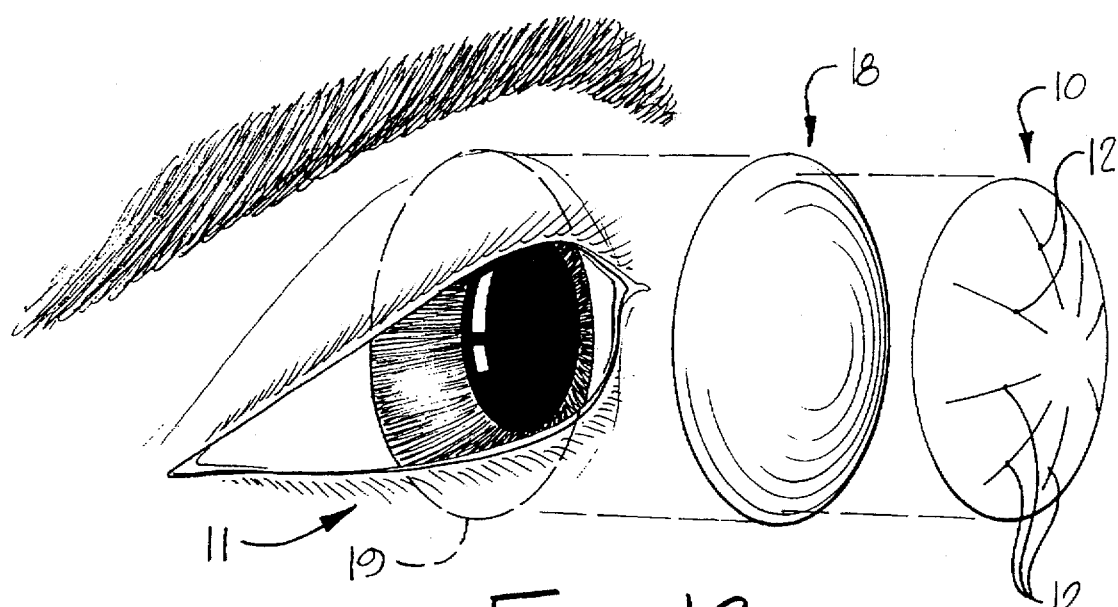
FIGS. 13 and 14 are views illustrating contact lenses of this invention worn piggyback, one lens over the other.
Figure 14:
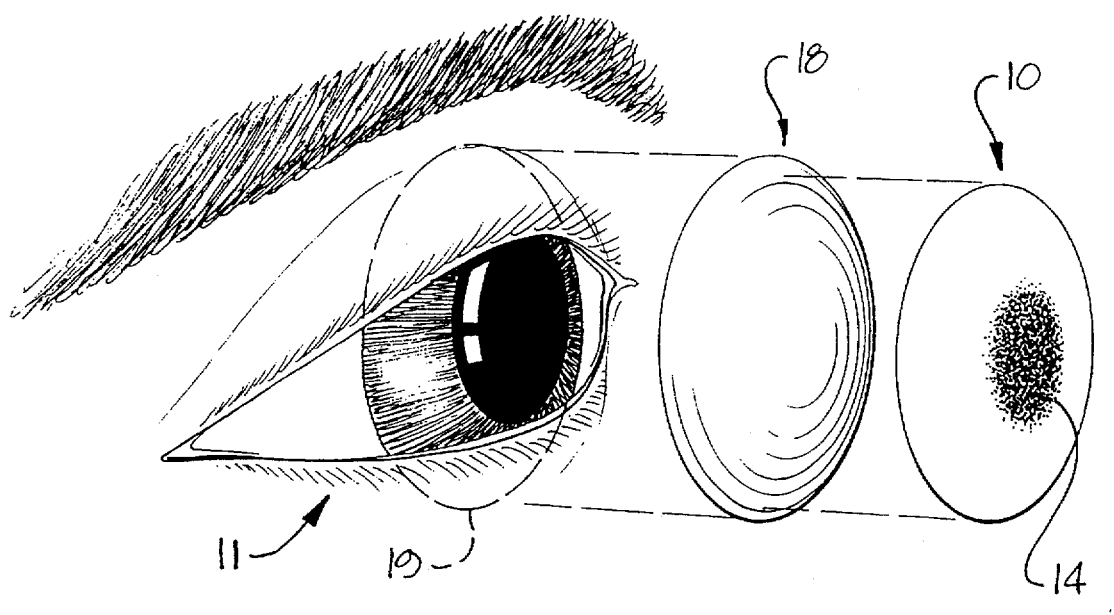

The contact lenses of the invention could be worn piggyback (FIGS. 13 and 14). That is the contact lens with the altered field of vision could be worn over the patient's prescription contact lens (FIGS. 13 and 14).

Figure 15:
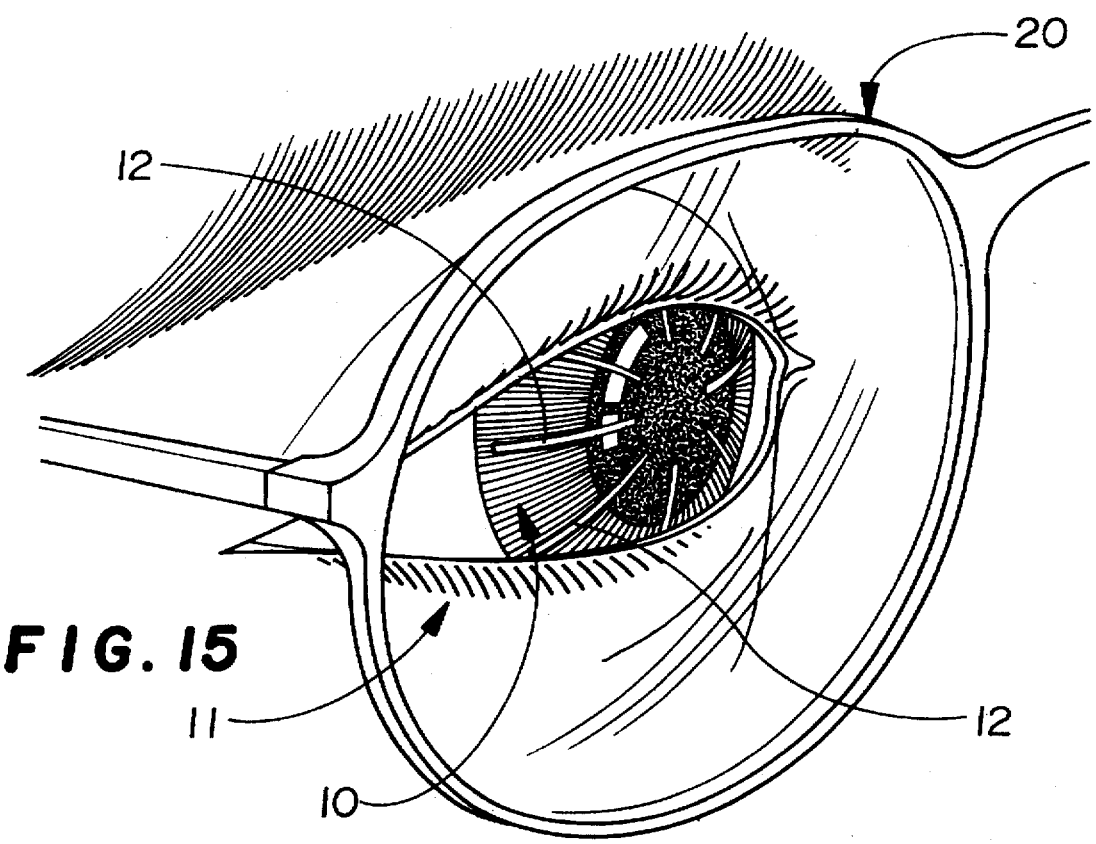
FIG. 15 is a view illustrating contact lenses of this invention worn under eyeglasses. The eyeglasses are only partially shown for ease of illustration.

With reference to FIG. 13 the contact lens of this invention 10 with radial lines 12 is worn over the patient's prescription contact lens 18, and in FIG. 14 the contact lens 10 with hazing 14 is worn over the patient's prescription contact lens 18. The dashed lines 19 in FIGS. 13 and 14 represent the area of placement of the contact lenses 10 and 18 in the eye 11. The contact lens 10 besides being worn in conjunction with prescription contact lenses 18, can be worn along with a patient's prescription eyeglasses 20 (FIG. 15). With the contact lens 10 worn piggyback over the patient's prescription CL 18, or in conjunction with prescription eyeglasses 20, the patient will be able to attain a more accurate assessment of possible visual aberrations prior to surgery and thereby give more meaningful informed consent.

Additional embodiments of this invention are possible as further exemplified.

The size of the optical zone can cause visual problems. A small optical zone may create halos, specially at night when the pupil may dilate to be larger than the optical zone. This problem is frequently seen with excimer PRK when used to correct higher degrees of myopia. This type of distortion may be simulated by limiting the optical zone of the contact lens to the maximum possible with PRK (approximately 6 mm with current technology). The 6 mm optical zone may be a blend with only the center of the zone (3 or 4 mm) possessing the full optical power required.

The accuracy of RK and PRK optical correction is limited. Some patients will have uncorrected vision of 20/20; however, some will have vision of 20/40. (Based on most studies for corrections of up to –6.00 diopters.) This is in part due to over and under corrections. Under corrections may be simulated by having a degree of residual myopia (perhaps –0.50 to –0.75 diopters from the ideal correction; eg. too weak a contact lens correction. Conversely, over corrections can be simulated by too strong a contact lens. These over and under corrections may be achieved by selecting a CL with slightly greater or lesser power than ideal or by having a small degree of plus or minus correction in a piggyback CL. An over correction of a myope would correct too much myopic or minus power, adding too much plus or hyperopic power, thus leaving the patient net plus.

Astigmatic correction deficiencies may be simulated with lenses that do not fully correct the astigmatism.

Each of the types of CL simulation may be used singly or in combination, either in a single CL or in a set of CL's.

A noteworthy embodiment of this invention envisions a set of modified contact lenses of this invention supplied in a kit. Lenses with radial lines, hazing, etc. would be included in the kit. The kit with the lenses would be convenient for supplying the doctor with contact lenses and could be supplied and used as an educational tool in the classroom. The kit and/or lenses may be disposable.

It is obvious to those skilled in the art that lenses with modified fields of vision simulating visual anomalies could be incorporated into a phoropter or trial lens set. The doctor could use such a device for obtaining informed consent from a patient.

Figure 16:
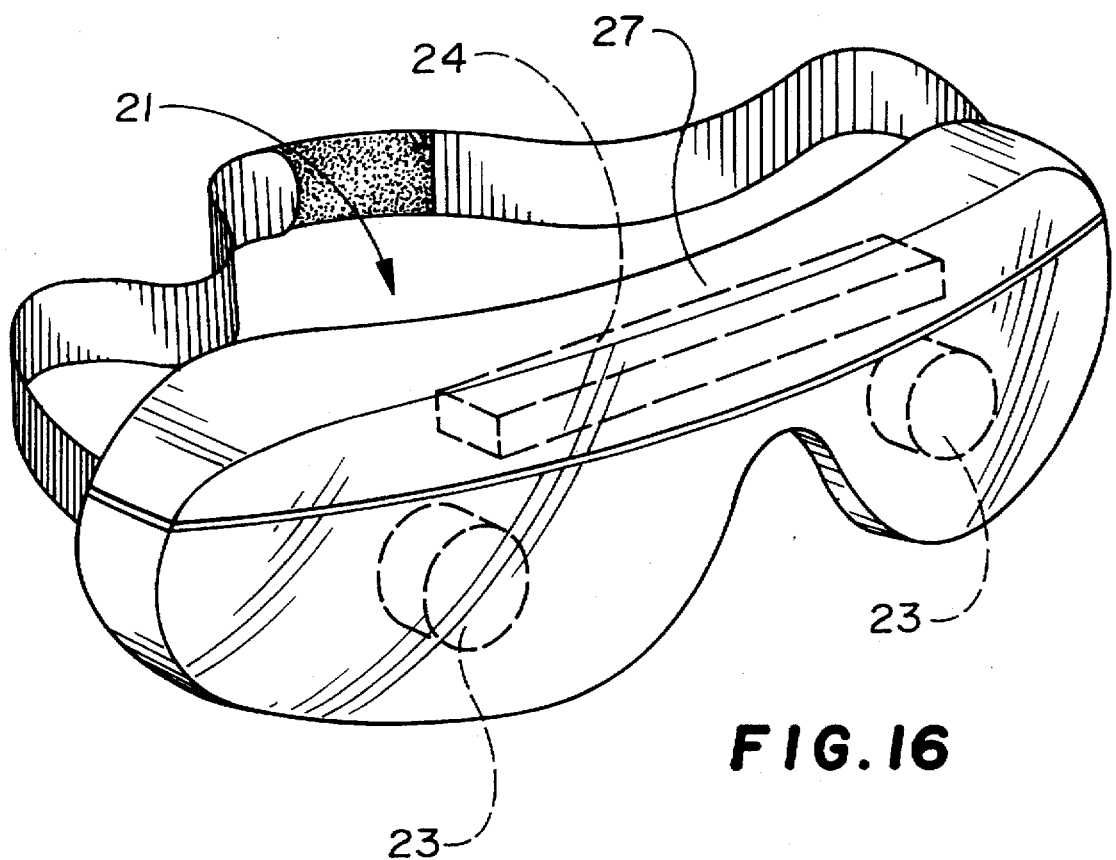
FIG. 16 is a front perspective view illustrating a pair of Virtual Reality Goggles.
Figure 17:
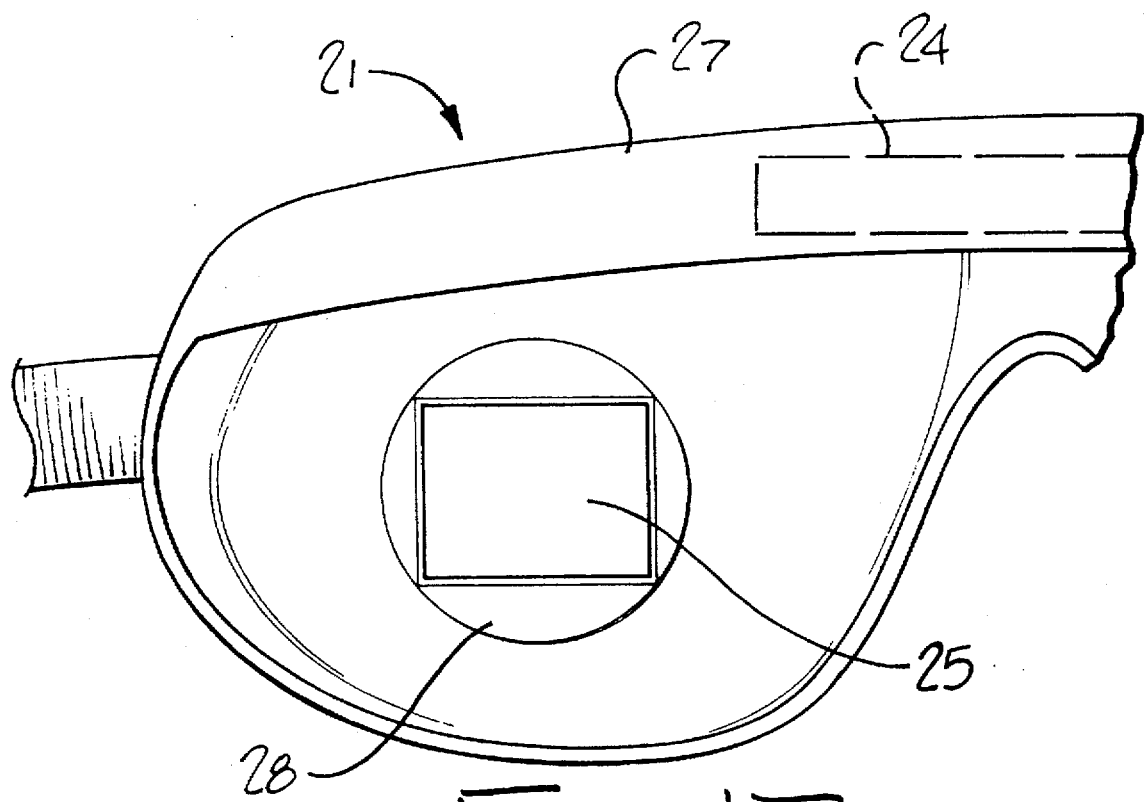
FIG. 17 is a rear elevational view thereof with part of the goggles broken away for ease of illustration.
Figure 18:
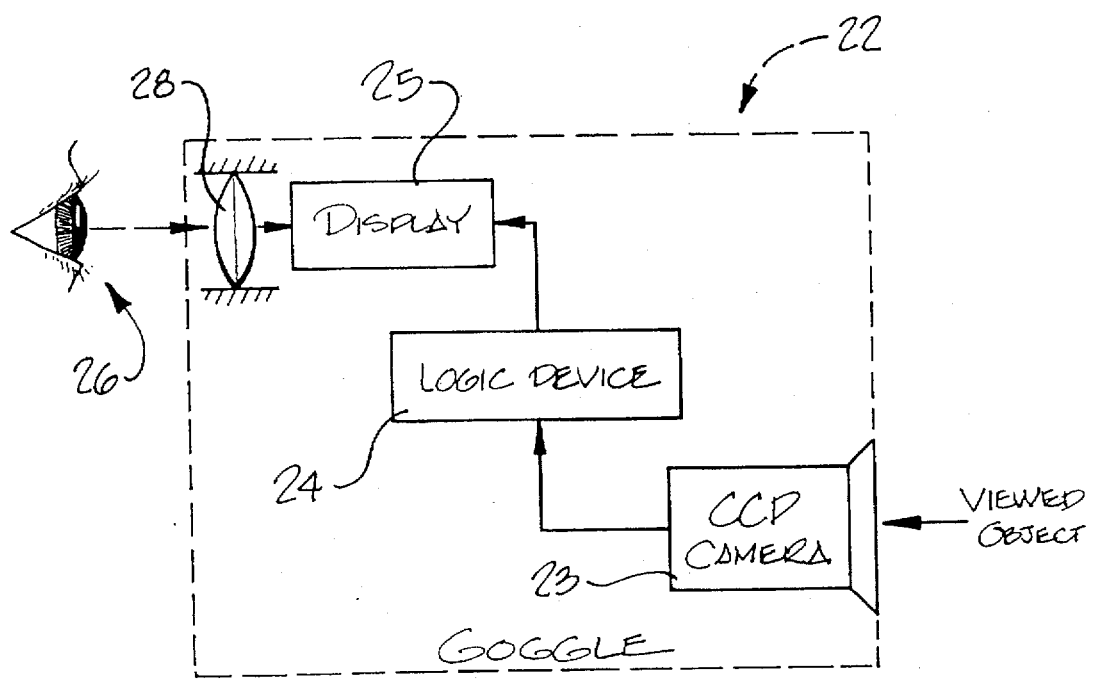
FIG. 18 is a block diagram representing the methodology employed in using Virtual Reality Goggles.

As a special and unique embodiment of this invention T.V. and computer program technology can be used to simulate visual disabilities described herein (FIGS. 16–18). Virtual Reality Goggles 22 (block diagram FIG. 18) may be constructed so that real time images from a T.V. camera (CCD) 23 are processed through software (logic device) 24 that creates the above described visual distortions which are displayed 25 in the goggles 22. In this embodiment the patient 26 would wear a virtual reality device or Virtual Reality Goggles 22 and the doctor would insert the program which would display on a T.V. screen in the goggles 25 the visual anomaly that could be expected as a result of the contemplated surgery. The Virtual Reality Goggles 22 are constructed so that real-time images from a T.V. camera (CCD) 23 are processed through software that creates the above described distortions which are displayed in the goggles 22.

The top of the glasses 27 houses the logic device 24. The eye piece of the glasses houses a small TV camera (CCD) similar to that used in children's video games ("Sega" T.M. style Virtual Reality Goggles). On the inside of the goggles there is a convex lens 28 to focus the image.

With reference specifically to the block diagram (FIG. 18) the patient 26 views the image through the convex lens 28 to focus on the display 25. The logic device 24 distorts the vision according to an algorithm for glare-loss of focus. The CCD 23 camera focuses on the viewed object.

With the use of Virtual Reality Goggles the doctor has an added dimension for obtaining informed consent from the patient.

Figure 19:
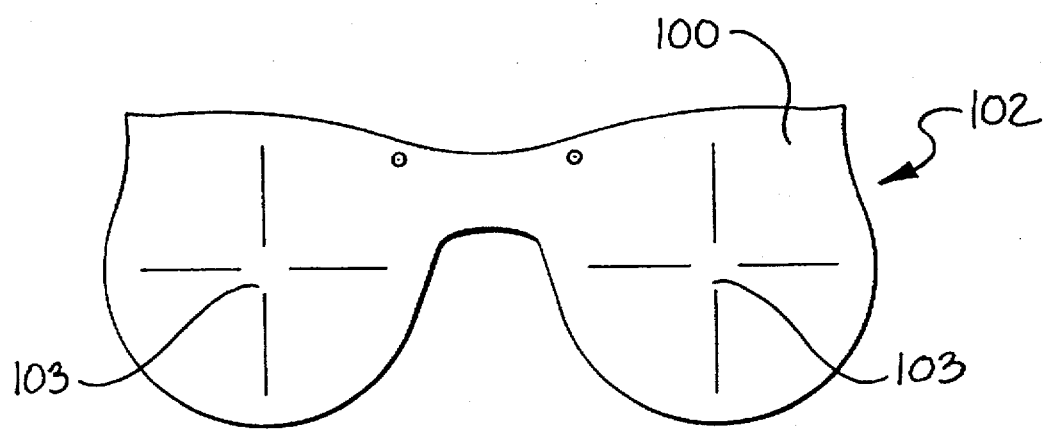
FIG. 19 shows a front view of clip-on glasses.
Figure 20:
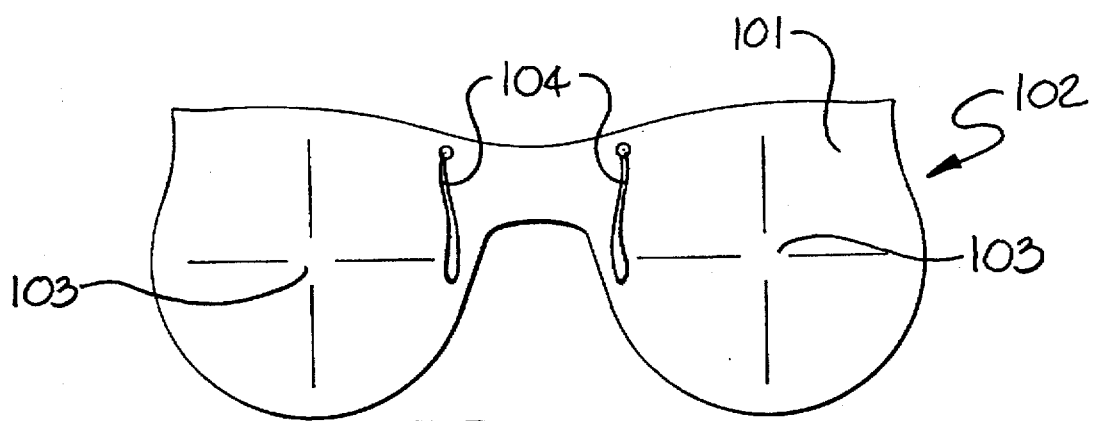
FIG. 20 is a rear view thereof.

With reference to FIGS. 19 and 20, there is illustrated the front view 100 and rear view 101, respectively, of clip-on glasses 102 with the line of sight modified to simulate starburst 103. The clips 104 are used to clip the clip-on glasses 102 to eyeglasses (not shown).

Figure 21:
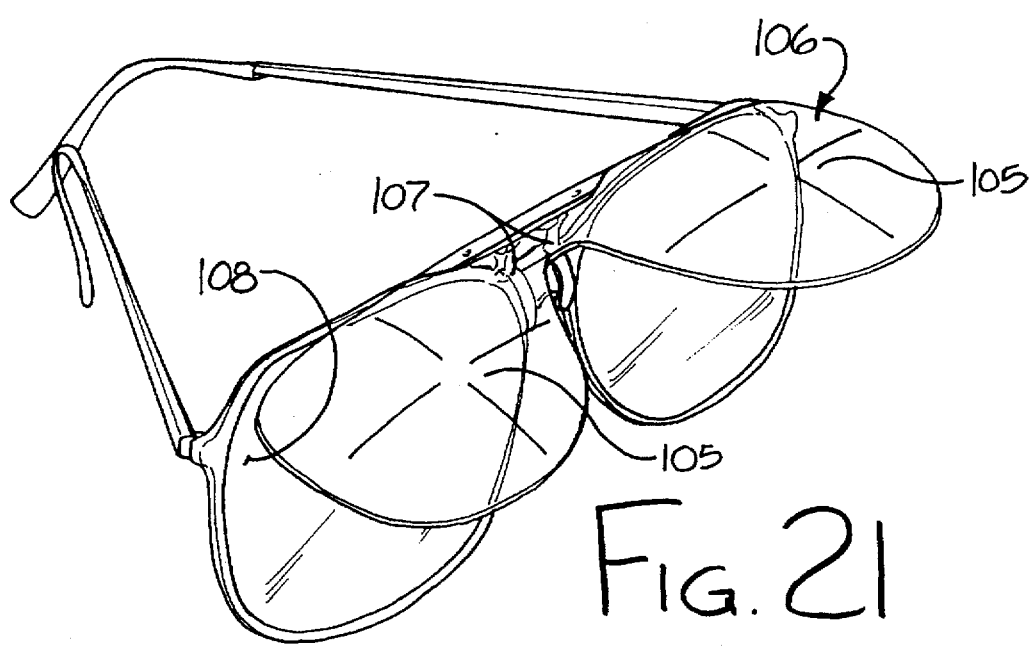
FIG. 21 is a view illustrating a hinged visor on glasses.

Referring now to FIG. 21 the modified lenses 105 can be a visor 106 hinged at 107 and attached to regular eyeglasses 108.

Figure 22:
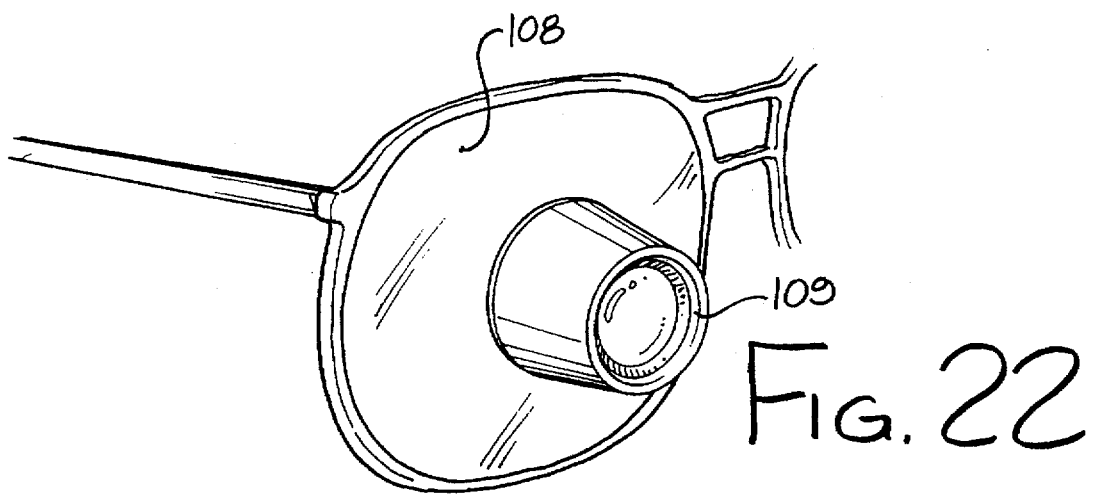
FIG. 22 is a view illustrating loupes to be fitted over eyeglasses.

The modified lenses can be fashioned into loupes 109 to be used in conjunction with eyeglasses 108 or spectacles 108 (only partially shown) (FIG. 22).

Figure 23:
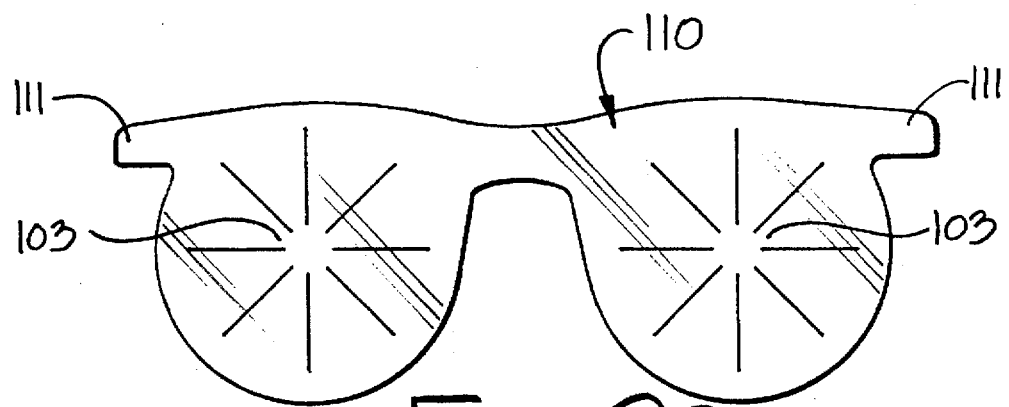
FIGS. 23–24 are front views of glasses for sliding behind a pair of worn eyeglasses.
Figure 24:

Slide behind lenses 110 with tabs 111 (FIGS. 23 and 24) can be worn in conjunction with eyeglasses (not shown). The line of sight has been modified to simulate starburst 103 or glare 112. These slide behind lenses 110 are generally made of plastic and are designed to slide behind the lenses of eyeglasses regularly worn by a patient.

Figure 25:
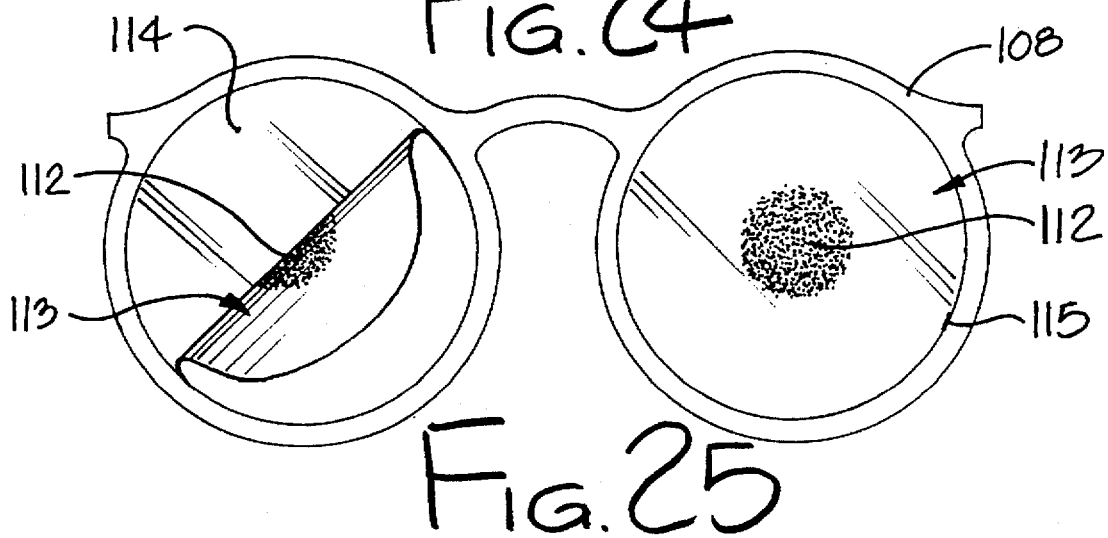
FIG. 25 is a view illustrating a modified thin transparent film press-on for application to eyeglasses.

A modified thin transparent film press-on 113 can be applied to the patient's own eyeglass 108, to produce visual distortion e.g. glare 112 (FIG. 25). In FIG. 25 the modified thin transparent film press-on 113 is being applied to the lens on the left 114 and is already in place as applied to the lens on the right 115.

Many advantages are envisioned by the use of the contact lenses of this invention. Primarily, the contact lenses when worn by the patient will simulate visual distortions that might be experienced postoperatively. Thus the informed consent from the patient after wearing the contact lenses will be more meaningful. This is so because the consent will be based on information derived from an objective physiological assessment, rather than a subjective verbal communication between doctor and patient. The use of contact lenses simulating postoperative visual defects may become the standard for legal informed consent in ophthalmologic surgery. Aside from being instructive to the patient, the contact lenses herein described are an educational aid. Student doctors, nurses and other interested parties, such as members of the family of a candidate for eye surgery could apply the contact lenses to objectively apprise themselves of possible postoperative visual deficiencies.

The benefits realized for the contact lenses herein described are equally applicable to the eyeglass modifications, as for example, clip-on glasses, hinged visor to be attached to regular eyeglasses, loupes, slide behind lenses and modified press-on thin film.

It would be clear to those skilled in the art that the eyeglasses of this invention can be fashioned as wrap-arounds. In addition, the lens can be placed in front of the patient's eye during examination as a trial lens. Stick-on lens, it is clear, can be adhesive or simply adhering plastic. The stick-on lens can be just about the size of the opacity or optical zone we are portraying.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for obtaining informed consent from a patient prior to ophthalmologic surgery comprising fitting over eyeglasses worn by said patient a lens or lenses whose field of vision has been modified to simulate a visual anomaly which may occur as a result of said surgery and then obtaining informed consent from said patient.

2. A method for obtaining informed consent from a patient prior to ophthalmologic surgery comprising fitting a pair of eyeglasses worn by said patient with slide-behind eyeglasses, eyeglasses having a clip or eyeglasses having a hinged clip whose field of vision has been modified to simulate a visual anomaly which may occur as a result of said surgery and then obtaining informed consent from said patient.

3. A method for obtaining informed consent from a patient prior to ophthalmologic surgery comprising fitting over eyeglasses worn by said patient a loupe having a lens whose field of vision has been modified to simulate a visual anomaly which may occur as a result of said surgery and then obtaining informed consent from said patient.

4. A method for obtaining informed consent from a patient prior to ophthalmologic surgery comprising fitting over eyeglasses worn by said patient one or more modified thin transparent film press-on's whose field of vision has been modified to simulate a visual anomaly which may occur as a result of said surgery and then obtaining informed consent from said patient.

* * * * *